(12) United States Patent
Wüllner et al.

(10) Patent No.: US 9,974,690 B2
(45) Date of Patent: May 22, 2018

(54) APPARATUS AND METHOD FOR LASIK

(75) Inventors: Christian Wüllner, Möhrendorf (DE); Klaus Vogler, Eckental (DE); Christof Donitzky, Eckental (DE)

(73) Assignee: Wavelight GmbH (DE)

( * ) Notice: Subject to any disclaimer, the term of this patent is extended or adjusted under 35 U.S.C. 154(b) by 1924 days.

(21) Appl. No.: 12/409,123

(22) Filed: Mar. 23, 2009

(65) Prior Publication Data
US 2010/0241108 A1 Sep. 23, 2010

(51) Int. Cl.
*A61F 9/008* (2006.01)

(52) U.S. Cl.
CPC .......... *A61F 9/008* (2013.01); *A61F 9/00804* (2013.01); *A61F 9/00836* (2013.01); *A61F 2009/00872* (2013.01)

(58) Field of Classification Search
CPC .. A61F 9/008; A61F 9/00804; A61F 9/00836; A61F 2009/00872; A61B 17/320783
USPC ................. 606/5, 4, 13, 10, 11, 17
See application file for complete search history.

(56) References Cited

U.S. PATENT DOCUMENTS

| | | | | |
|---|---|---|---|---|
| 4,988,348 A | * | 1/1991 | Bille | 606/5 |
| 6,027,494 A | * | 2/2000 | Frey | 606/5 |
| 6,280,435 B1 | * | 8/2001 | Odrich et al. | 606/5 |
| 6,293,938 B1 | * | 9/2001 | Muller | A61F 9/008 128/898 |
| 6,312,424 B1 | * | 11/2001 | Largent | 606/5 |

(Continued)

FOREIGN PATENT DOCUMENTS

| | | |
|---|---|---|
| DE | 10354025 | 6/2005 |
| EP | 1570822 | 9/2005 |

(Continued)

OTHER PUBLICATIONS

Patent Cooperation Treaty—European Patent Office, "Notification of Transmittal of the International Search Report and the Written Opinion of the International Searching Authority, or the Declaration," International Application No. PCT/EP2009/002123, dated Oct. 5, 2009, 16 pages.

(Continued)

*Primary Examiner* — Corrine McDermott
*Assistant Examiner* — Tin Nguyen
(74) *Attorney, Agent, or Firm* — Keiko Ichiye

(57) ABSTRACT

An apparatus for LASIK is equipped with the following:
 a first laser radiation source for generating first laser radiation pulses;
 first means for guiding and shaping the first laser radiation pulses;
 a second laser radiation source for generating second laser radiation pulses;
 second means for guiding and shaping the second laser radiation pulses;
 a controller with:
  a first treatment program for controlling the first means and the first laser radiation pulses for the purpose of producing an incision in the cornea, the first treatment program generating regular corneal surface structures;
  a second treatment program for controlling the second means and the second laser radiation pulses for the purpose of reshaping the cornea and changing its imaging properties; and
  a third treatment program which controls the second means and the second laser radiation pulses for the purpose of removing the aforementioned regular structures.

22 Claims, 2 Drawing Sheets

(56) References Cited

U.S. PATENT DOCUMENTS

Figure 1:
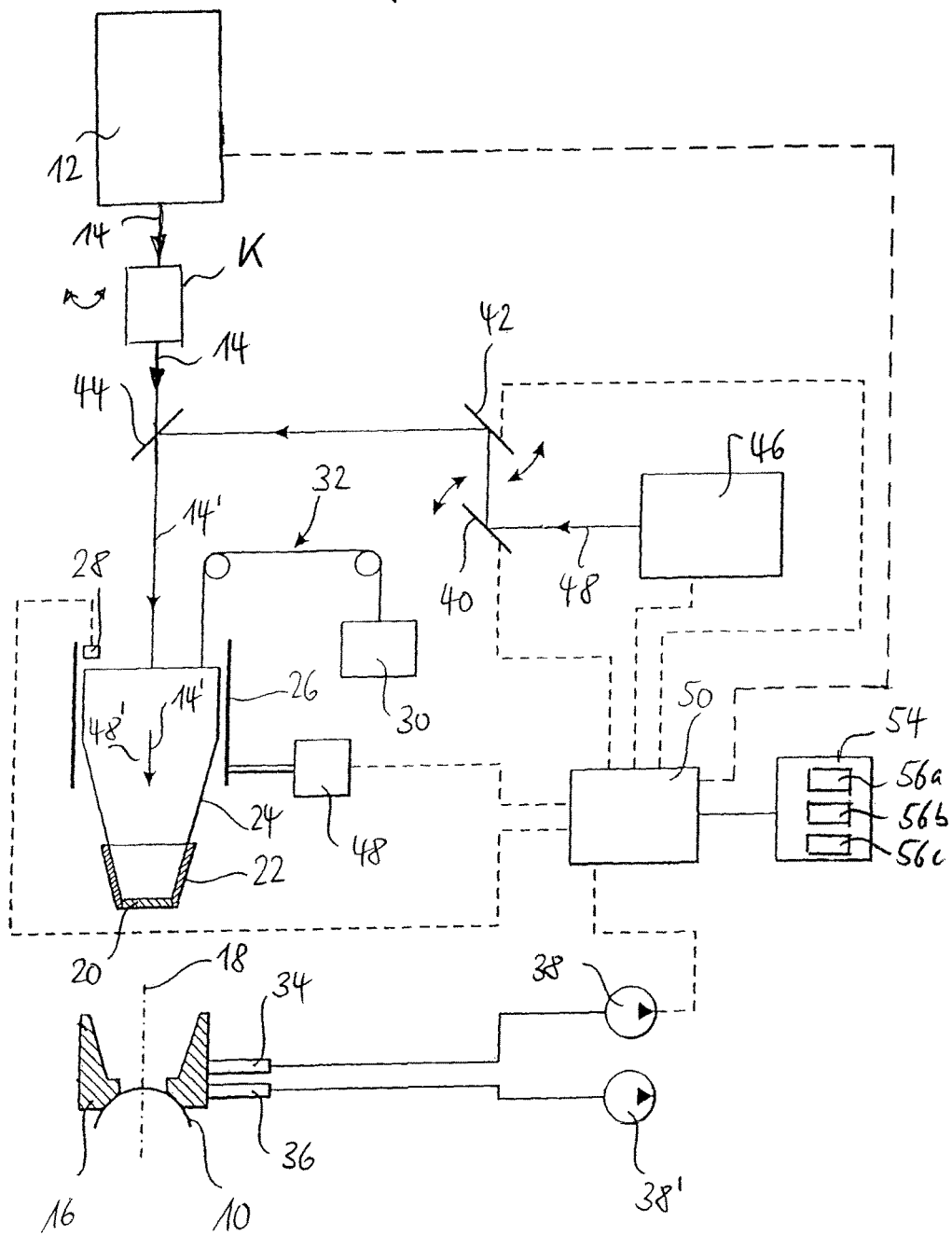

| | | | |
|---|---|---|---|
| 6,325,792 B1* | 12/2001 | Swinger et al. ............... 606/4 | |
| 2001/0046132 A1* | 11/2001 | Lanzetta et al. ............ 362/276 | |
| 2001/0056277 A1* | 12/2001 | Vinciguerra et al. ............ 606/5 | |
| 2003/0069566 A1* | 4/2003 | Williams ............ A61F 9/00804 | |
| | | | 606/5 |
| 2003/0176855 A1* | 9/2003 | Gross ..................... A61F 9/008 | |
| | | | 606/5 |
| 2004/0243112 A1 | 12/2004 | Bendett et al. | |
| 2005/0085800 A1* | 4/2005 | Lenzner et al. ................. 606/5 | |
| 2007/0027439 A1* | 2/2007 | Durrie et al. .................... 606/5 | |
| 2007/0093795 A1 | 4/2007 | Melcher et al. | |
| 2008/0071254 A1 | 3/2008 | Lummis et al. | |
| 2010/0331831 A1* | 12/2010 | Bischoff ................ A61F 9/008 | |
| | | | 606/5 |

FOREIGN PATENT DOCUMENTS

| | | |
|---|---|---|
| EP | 1792593 A1 | 6/2007 |
| JP | 2000300596 A | 10/2000 |
| JP | 2000513986 A | 10/2000 |
| WO | 9934742 A1 | 7/1999 |
| WO | 03011175 A2 | 2/2003 |
| WO | WO2008122405 A1 | 10/2008 |
| WO | WO-2010/022745 | 3/2010 |

OTHER PUBLICATIONS

Ronald R. Krueger, MD, MSE, et al., "Rainbow Glare as an Optical Side Effect of IntraLASIK," 2008 American Academy of Ophthalmology, Published by Elsevier Inc., ISSN 0161-6420/08/$, pp. 1187-1195.

PCT International Search Report for PCT/EP2008/006962, dated Apr. 27, 2009, 6 pages.

Russian Patent Office, "Examination report" for Application No. 2011139568, dated Mar. 18, 2013, 5 pages with translation.

Japanese Patent Office, "Notification for Reasons of Refusal" for Application No. 2012-501134, dated Jun. 14, 2013, 4 pages with translation.

* cited by examiner

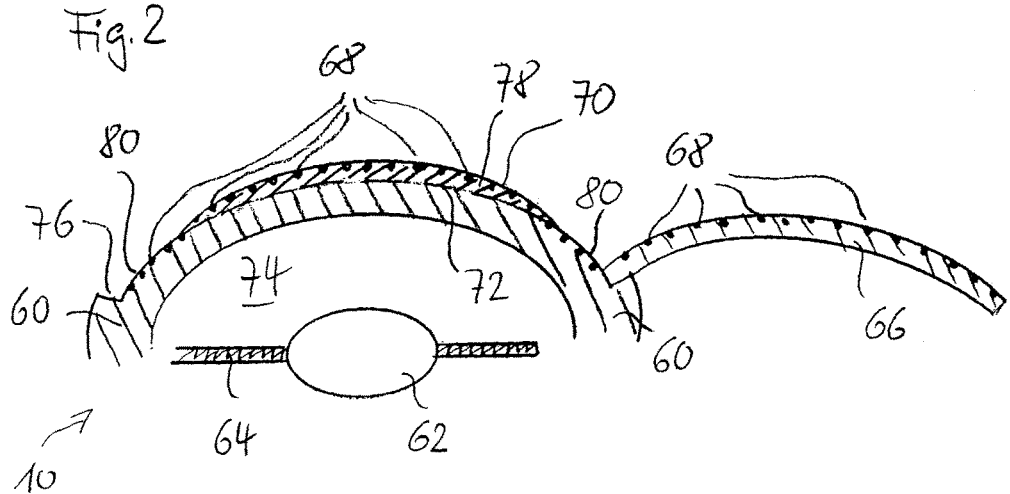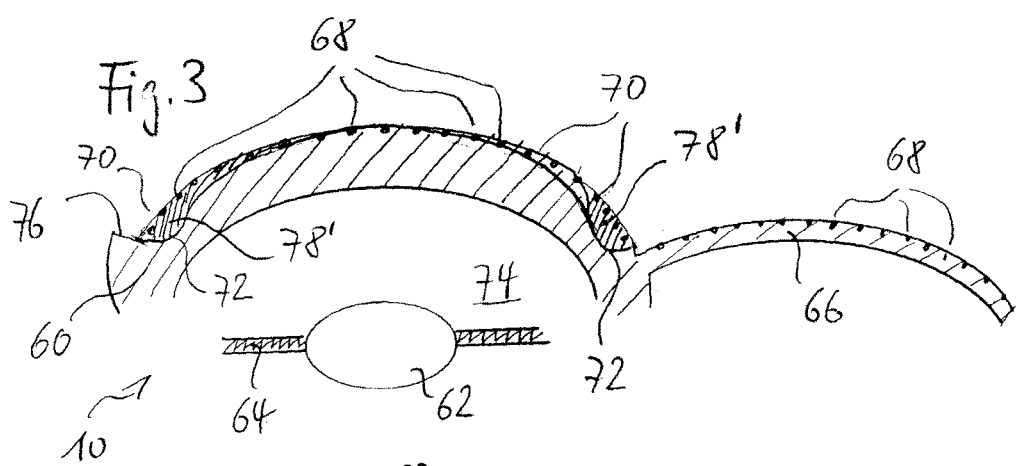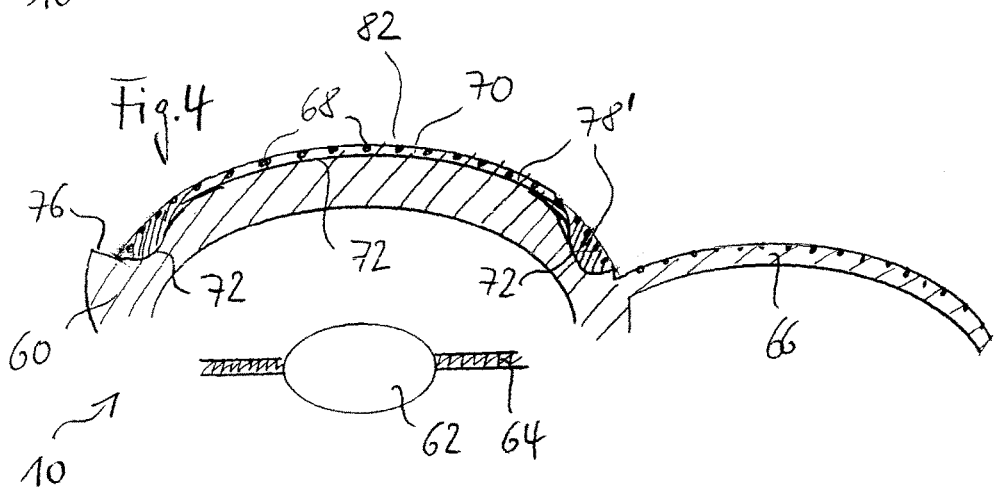

APPARATUS AND METHOD FOR LASIK

The invention relates to an apparatus and a method for laser in-situ keratomileusis (LASIK).

In refractive ophthalmological surgery the refractive properties and imaging properties of the eye are changed by interventions in respect of the eye of a patient for the purpose of correcting or alleviating sight defects. Known, in particular, is the LASIK process, wherein the cornea of the eye is reshaped. In the conventional LASIK process, in a first step a flat corneal incision is made with a mechanical microkeratome, in order in this way to produce a so-called flap which remains firmly connected to the cornea on one side, so that it can be folded upwards in order to expose underlying corneal tissue (stroma). In the exposed stroma the ablation—that is to say, the removal of tissue by means of, ordinarily, excimer-laser radiation—is then carried out, whereupon the flap is then folded back and heals up. In this process the epithelium remains largely uninjured and the healing process takes place relatively quickly and in pain-free manner. In a conventional mechanical microkeratome a sharp blade oscillates.

For the purpose of cutting the flap, the mechanical microkeratome has recently been increasingly replaced by laser radiation. The laser radiation is focused below the surface of the cornea and guided on a trajectory, the power densities being so high that a continuous incision arises by virtue of photodisruptive effects. In order to obtain the high power densities, short laser pulses within the femtosecond range are employed, for which reason this process is also designated as fs LASIK.

In the case of the aforementioned fs LASIK, in the course of cutting the flap a dense succession of aligned (micro) disruptions occurs by reason of the highly focused laser radiation pulses of high power density. Overall a two-dimensional continuous incision arises in the stroma of the cornea. Via the remaining hinge the flap is then folded aside, and the actual LASIK then takes place—that is to say, the ablation (removal) of corneal tissue in the open stroma in accordance with a defined treatment program for resection of a defined ablation volume for the purpose of reshaping the cornea.

The production of the flap in the case of fs LASIK has a number of advantages in comparison with the use of conventional mechanical microkeratomes and is therefore increasingly gaining acceptance. In the case of fs LASIK (sometimes also designated as fs microkeratome), the depths of cut can be adhered to exactly in the desired manner with very small fluctuations, and special marginal incisions with defined angles can also be formed which, in particular, bring advantages with regard to the biomechanical stability of the flap that has been folded back.

However, sometimes in the course of the fs-LASIK incision side-effects disturbing the patient may also occur in the form of the so-called rainbow-glare effect. This effect, which is felt to be annoying by some patients, consists in the perception of colour dispersions when observing certain structures and sharp edges. The cause of this annoying rainbow-glare effect is the generation of a type of grating structure in the incision surface for the production of the flap that has arisen by virtue of the photodisruption. The individual laser spots are typically placed so regularly that regular two-dimensional gratings with grating constants within the µm range may arise at least in certain regions of the incision, which may then continue to exist in the healed eye also after conclusion of the LASIK procedure and may then cause the known grating effect—that is to say, a colour-resolved dispersion in the sense described above. Frequently the refractive ablation—that is to say, the targeted removal of corneal tissue for the purpose of reshaping the cornea with desired imaging properties—does also bring about a removal of the aforementioned undesirable grating structures, but this is successful, as a rule, only in those regions of the cornea in which a relatively 'large' amount of tissue is resected, whereas in those corneal regions in which the refractive ablation (that is to say, the removal of the desired ablation volume for the purpose of correcting the imaging properties) does not resect so much tissue the undesirable grating structures in the cornea frequently remain, for example in the central corneal region in the case of hyperopia correction.

In EP-A 1 977 725 this problem is countered by the regularity of the spot positions of the laser radiation in the course of producing the incision being cancelled to such an extent that the undesirable regular grating structure does not arise. A stochastic 'wobbling' of the mirrors controlling the radiation is implemented therein, in order to avoid the undesirable regular grating structures in the course of producing the flap incision. However, despite these stochastic fluctuations of the spot positions, it has to be guaranteed that the incision passes through continuously and a sufficiently smooth surface in the exposed stroma is guaranteed. In the aforementioned known process this requires a very elaborate optimisation and control.

The object underlying the invention is to avoid the occurrence of the so-called rainbow-glare effect with means that are as simple as possible in the case of fs LASIK.

An apparatus according to the invention is equipped with
 a first laser radiation source for generating first laser radiation pulses having a power density for bringing about disruption in corneal tissue,
 first means for guiding and shaping the first laser radiation pulses into the corneal tissue,
 a second laser radiation source for generating second laser radiation pulses having a power density for bringing about ablation of corneal tissue,
 second means for guiding and shaping the second laser radiation pulses in relation to the cornea,
 a controller with a first treatment program for controlling the first means and the first laser radiation pulses for the purpose of producing an incision in the cornea, and with
 a second treatment program for controlling the second means and the second laser radiation pulses for the purpose of reshaping the cornea and changing its imaging properties, wherein
 the first treatment program generates regular corneal surface structures which cause a rainbow-glare effect in connection with the imaging properties of the cornea,
 characterized by
 a third treatment program which controls the second means and the second laser radiation pulses for the purpose of removing the aforementioned regular structures.

In the case of the apparatus described above, the aforementioned "regular corneal surface structures", which bring about a rainbow-glare effect, are to be understood as being those structures which in the course of making the incision for the flap generate in undesirable manner a grating structure in the sense described above and therefore in accordance with the invention are separately removed or at least so greatly reduced with the treatment program which subsequently brings about in the stroma the ablative shaping by resection of the so-called ablation volume that the aforementioned rainbow-glare effect disappears. In this sense the ablation volume is to be understood as being that volume of the cornea which has been calculated in advance for the refractive surgery in order to bring about the desired change in the imaging of the eye overall. But, in accordance with the invention, going beyond that, a smoothing is provided of the stromal surface that is exposed after the flap has been folded back in those regions in which undesirable grating structures have arisen in the course of the flap incision, this smoothing having nothing significant to do with the change in the refractive properties (imaging properties) of the eye.

The invention may also be described in such a way that in addition to the PRK—that is to say, the photorefractive keratectomy (in the course of which as a result of reshaping of the cornea the imaging properties thereof are changed) a PTK is provided—that is to say, a phototherapeutic keratectomy, in the course of which relatively superficially situated defects, scars and other surface structures are removed. The latter procedure serves in the invention for removal of the aforementioned grating structures on the surface of the exposed stroma.

This removal is effected in the course of the photoablation in a separate step, together with the refractive reshaping of the cornea for the purpose of changing the imaging properties thereof.

The patent claim as reproduced above differentiates first, second and third treatment programs having the respectively specified functions. This differentiation is to be understood as being functional—i.e. the three stated functions of the three treatment programs may be combined in a single computer program, or the second and third treatment programs, which bring about the ablative effects, may be combined with one another in a single program.

In the case of a LASIK myopia treatment the cornea is normally flattened—i.e. the radius of curvature of the cornea is increased. This means that the ablation volume is situated mainly in the middle region of the cornea—that is to say, around the optical axis—whereas in the outer regions of the cornea no tissue or only little tissue is resected. But, as a rule, the flap is cut over a very wide region of the cornea, so that in the case of treatment of myopia the grating structures generated by the flap incision in the marginal regions of the exposed stroma cannot, under certain circumstances, be totally removed by the subsequent resection of ablation volume from the stroma, whereby according to the invention in these outer regions of the cornea close to the marginal flap incision the risk of undesirable grating structures remaining in the corneal issue is particularly high and therefore according to the invention, in addition to the resection of the refractive ablation volume, a smoothing ablation is also effected in the marginal regions of the cornea.

On the other hand, in the case of LASIK treatment of hyperopia the ablation volume is normally calculated in such a way that the radius of curvature of the cornea is reduced—that is to say, in the marginal regions of the cornea, close to the marginal flap incision, normally more corneal tissue is ablated than in central, middle regions of the cornea. Therefore there is the risk that without the invention in the course of the hyperopia treatment undesirable grating structures that have arisen in middle regions of the cornea in the course of the flap incision remain and in this way bring about a strong rainbow-glare effect. Therefore in the case of hyperopia treatment the invention provides that, over and beyond the marginal ablation volume that is stipulated for the refractive correction of the cornea, in addition a smoothing ablation is carried out for the purpose of removing the grating structures also in middle regions of the cornea.

Exemplary embodiments of the invention will be elucidated in more detail in the following on the basis of the drawing. Shown are:

FIG. 1 schematically, an apparatus for implementing an fs LASIK;

FIG. 2 schematically, a section through the cornea of an eye for the purpose of elucidating a myopia treatment;

FIG. 3 a schematic section through the cornea of an eye for the purpose of elucidating a hyperopia treatment; and FIG. 4 a section corresponding to FIG. 3, including the target surface striven for in accordance with the invention.

FIG. 1 shows an apparatus for fs LASIK, wherein ordinarily two different sources of laser radiation are employed, namely a first laser radiation source for the purpose of generating femtosecond pulses for the implementation of the flap incision by photodisruption and a second laser radiation source for the purpose of generating laser radiation pulses of another type having a lower power density for the purpose of implementing the ablation of corneal tissue. Ordinarily in the state of the art two different laser-radiation systems with separate optical systems for beam shaping and beam guidance in relation to the eye are provided for this purpose, which are alternatively (independently of one another) aligned in relation to the eye to be treated. In FIG. 1, however, the two systems have been represented in virtually combined manner for the sake of simplicity.

A first laser radiation source 12 serves for generating femtosecond pulses 14 which are known as such in this technology and which have such a high power density that after focusing in the interior of the cornea they bring about a disruptive effect there. The means for shaping and guiding these first laser radiation pulses 14 are indicated in FIG. 1 synoptically by reference symbol K and are known as such in the state of the art. Via a mirror 44 which is transmitting in respect of the first laser radiation pulses 14 this laser radiation is guided in the direction towards the eye 10. The eye 10 is fixed by means of a suction ring 16, and an applanation lens 20 is lowered coaxially relative to the axis 18 of the suction ring 16, downwards in the Figure, so that an interface unit 22 engages in a conical socket on the suction ring 16. By means of focusing optics 24, the first laser radiation pulses 14' for generating the flap incision in a manner known as such are focused into a previously calculated surface below the surface of the cornea of the eye 10. The focusing optics 24 are guided in a mount 26. The guidance is effected by means of a location sensor 28, the focusing optics 24 being suspended in freely hanging manner via a counterweight 30 and a rocker, in order to enable a coupling, which places virtually no burden on the eye, of the interface unit 22 onto the eye 10. The suction ring 16 is fixed by means of pipe connections 34, 36, known as such, and vacuum pumps 38. The focusing optics 24 described above serve mainly for the focusing of the second laser radiation pulses, described below, for the ablation. For the first laser radiation pulses 14, optical shaping means and guidance means for the radiation are provided which are known as such in the state of the art and are indicated in FIG. 1 by function block K, as a result of which the control of the foci of the first laser radiation pulses in space and time is then also effected in known manner.

A second laser radiation source 46 serves for generating second laser radiation pulses 48 for the ablation. These second laser radiation pulses 48 are directed into the focusing optics 24 via mirrors (including scanner mirrors) 40, 42, 44 known as such. Details of this arrangement are elucidated in more detail in international patent application PCT/EP2008/006962, which is included here in full by reference.

A computer controller 50 controls all the controllable components of the system, the control connections being indicated in FIG. 1 by dashed lines.

In a memory 54 there are stored, in particular, a first treatment program 56a, a second treatment program 56b and a third treatment program 56c, which the controller 50 can access alternatively. These three treatment programs will be described in more detail below.

With the first treatment program 56a the computer controller 50 controls the laser 12 and the first laser radiation pulses 14 generated thereby for the purpose of implementing the flap incision that has been described by means of photodisruption. This is known as such in the state of the art, as is the phenomenon that in the process undesirable grating structures in the above sense are generated on the surface of the stroma that is exposed after the flap has been folded back.

For the subsequent ablation of corneal tissue for the purpose of implementing the PRK, the computer controller 50 accesses the second treatment program 56b, so that an ablation volume that has been calculated in advance in known manner is ablated out of the stroma of the cornea, in order to modify the imaging properties of the cornea in desired manner.

The undesirable grating structures that are possibly generated when executing the first treatment program 56a are then removed in a third step in accordance with a third treatment program 56c (PTK). This is described in more detail on the basis of FIGS. 2 to 4.

FIGS. 2 to 4 show the cornea 60 of an eye 10 schematically in section. Represented are only the parts of the eye that are of greater interest here (the retina etc. have accordingly been omitted).

Shown, in addition to the cornea 60, are the crystalline lens 62 and the iris 64.

With the first treatment program 56a, by means of the first laser radiation source 12 the flap incision of the fs LASIK is implemented in a manner known as such. In the process the undesirable grating structures, elucidated above, arise, which are indicated schematically in the Figures by reference symbol 68—that is to say, depressions in the respectively exposed surface of the corneal tissue having, by reason of their regular structure, the undesirable effects that have been described. This grating-like structure typically has a grating constant within the μm range, with the consequences elucidated above with regard to rainbow glare. Reference symbol 68 accordingly indicates a so-called micrograting.

In the Figures the initial surface of the stroma which is exposed after the flap 66 has been folded back is denoted by 70. According to FIG. 2, the micrograting that is formed from the depressions 68 is accordingly distributed over the entire exposed surface of the stroma of the cornea. In the exemplary embodiment according to FIG. 2, myopia is to be treated—that is to say, the radius of curvature of the cornea after the treatment is to be increased, so the cornea is to be flattened. This is represented in FIG. 2 by the ablation volume 78 (closely hatched)—that is to say, that volume of the cornea which is to be resected by ablation by means of the second laser radiation pulses 48. The target surface that is striven for in this case is provided with reference symbol 72. Consequently the ablation volume 78 in FIG. 2 is the closely hatched region between the initial surface 70 and the target surface 72. In the case of myopia treatment, in the middle region of the cornea the depressions 68 forming the micrograting therefore disappear almost by themselves, since sufficient corneal tissue is resected in order to cause the undesirable grating structure largely to disappear at the end. Therefore in the case of a typical myopia treatment it is not absolutely necessary to provide in this middle region of the cornea separate measures for smoothing the surface and for removing the undesirable grating structure (although, in accordance with the invention, this is not excluded). However, as FIG. 2 shows, in marginal regions 80 of the exposed stromal bed the undesirable microstructure formed by the depressions 68 is largely preserved even after implementation of the ablation, so that in marginal regions 80 of the cornea—that is to say, close to the marginal flap incision 76—special measures for removing the micrograting generated by the depressions 68 are required. For this purpose the computer controller 50 has recourse to the third treatment program 56c, which guides the second laser radiation pulses 48 over the exposed surface of the stroma in such a way that the surface is smoothed also in the marginal regions 80. For this purpose, processes—known as such—of phototherapeutic keratectomy (PTK) can be called upon—see, for example, A. N. Kollias et al., Journal of Refractive surgery, Vol. 23, September 2007, pp 703-708, or Arch. Ophthalmology, Vol. 109, June 1991, pp 860-863 or P. Vinciguerra, F. Camesasca, Journal of Refractive Surgery, Vol. 20, 2004, pp 555-563. To this end, recourse may be had to the cited known processes of PTK.

In modification of the exemplary embodiments described above, this smoothing of the stromal surface that is exposed after the flap has been folded back may also be implemented not by the third treatment program with laser radiation but rather by other PTK techniques, for example by a manual smoothing, for example of the marginal regions 80 in the exemplary embodiment according to FIG. 2, with application of suitable liquids (see the cited literature) and, for example, with a brush. In this variant of the invention the undesirable micrograting is accordingly 'ground away' mechanically (without laser radiation).

After removal of the undesirable grating structure and folding-back of the flap 66, it is normally ensured that no undesirable grating structure finally remains in the refractively amended corneal tissue. Microstructures possibly remaining on the inside of the flap are not sufficient to form the undesirable microstructure, or do not come to be situated exactly above the original grating structures after the flap has been folded back, so that the smoothing measures described above with respect to the stromal surface are sufficient. It has been proved experimentally that grating structures possibly remaining in the flap are less critical than the grating structures in the stroma, described above. This is explained by the fact that in the course of photodisruption the fs pulses in the direction of propagation of the radiation have a relatively sharp start. In the case of LIOB (laser-induced optical breakdown), therefore, the depressions remaining in the flap are distinctly less pronounced (deep) than in the stromal bed. The depressions in the flap are typically less deep than 5 μm, whereas the depressions in the stromal bed are distinctly deeper and almost attain the Rayleigh length (15 μm to 20 μm). Alternatively, the undesirable grating structures 68 in the flap 66 may also be removed mechanically in the manner described above.

FIG. 3 shows the treatment of a hyperopia with fs LASIK, parts corresponding to one another having been provided with identical reference symbols in all the Figures. As already elucidated above, in the case of hyperopia treatment the ablation volume 78' is situated mainly in the marginal regions of the exposed stroma—that is to say, close to the marginal flap incision 76, this being represented in FIG. 3 by the closely hatched regions that mark the ablation volume 78'. As a result of removal of the ablation volume 78' by means of the second laser radiation pulses 48, the undesirable grating structures 68 also disappear in these regions, whereas in the middle region these structures are largely preserved in the initial surface 70, as FIG. 3 represents. Therefore in the case of the hyperopia treatment according to FIG. 4 also in the middle region 82 of the stroma which is exposed after the flap 66 has been folded back a smoothing is carried out to the effect that the microgratings 68 disappear and a smooth target surface 72 is obtained. The PTK techniques elucidated in more detail above—that is to say, either the third treatment program 56c or even other PTK smoothing techniques according to the literature cited above—serve for this purpose.

If the third treatment program 56c is employed, then in particular in the middle region of the exposed stroma a layer between the initial surface 70 and the target surface 72 is resected having a thickness of up to 10 µm, this being capable of being implemented effectively with the excimer laser 46 via the computer controller 50. A flap 66 is typically 100-160 µm thick.

In this connection the ablation serving for smoothing with the third treatment program can be taken into account in the second treatment program which brings about the refractive correction of the cornea—i.e. when calculating the ablation volume and accordingly when generating the second treatment program for the photoablation it can be taken into account from the outset that a uniform resection of tissue occurs over the entire corneal surface or over selected parts of the corneal surface (in the case of FIG. 4, accordingly the middle region 82). Analogous remarks apply to the myopia treatment according to FIG. 2, in which over the entire exposed surface of the stroma or even parts thereof (such as, in particular, the marginal regions 80 according to FIG. 2) a smoothing resection of tissue occurs which is taken into account in the second treatment program for the calculation of the refractive effect.

The invention claimed is:

1. Apparatus for laser in-situ keratomileusis (LASIK), with:
    a first laser radiation source for generating first laser radiation pulses having a power density configured for bringing about disruptions in corneal tissue,
    a second laser radiation source for generating second laser radiation pulses having a power density configured for bringing about ablation of corneal tissue,
    a controller configured to:
        control application of the first laser radiation pulses for generating an incision in a cornea, the application of the first laser radiation pulses producing undesired grating structures in first and second regions of the cornea that cause a rainbow-glare effect associated with the cornea;
        control application of the second laser radiation pulses for reshaping the cornea and changing its refractive properties in a desired manner to correct refractive errors, wherein reshaping the cornea includes the removal of an ablation volume from the first region of the cornea but not the second region of the cornea and wherein removal of the ablation volume includes removal of the undesired grating structures from the first region of the cornea, but not from the second region of the cornea such that the undesired grating structures remain in the second region of the cornea; and
        control the application of the second laser radiation pulses for removing the undesired grating structures in the second region of the cornea to minimize the undesired rainbow glare effect of the eye without causing undesired changes in the first region of the cornea and without changing the refractive properties of the eye, wherein the removing the undesired grating structures includes removing a volume from the second region of the cornea but not the first region of the cornea, and wherein the first region and second region do not overlap.

2. The apparatus according to claim 1 for LASIK treatment of myopia, wherein the first region of the cornea is a middle region of the cornea and the second region of the cornea is a marginal region of the cornea.

3. The apparatus according to claim 1 for LASIK treatment of hyperopia, wherein the first region of the cornea is a marginal region of the cornea and the second region of the cornea is a middle region of the cornea.

4. The apparatus according to claim 1, wherein the ablation volume is calculated to achieve a desired refractive effect by taking into account the removal of tissue in the second region of the cornea associated with removing the regular corneal surface structures in the second region of the cornea.

5. The apparatus according to claim 1, wherein removing the regular corneal surface structures in the second region of the cornea comprises resecting a tissue layer having thickness up to 10 µm.

6. The apparatus according to claim 1, wherein controlling the application of the second laser radiation pulses for reshaping the cornea and changing its refractive properties and controlling the application of the second laser radiation pulses for removing the undesired grating structures in the second region of the cornea are combined in a single computer program executable by the controller.

7. The apparatus according to claim 6, wherein controlling the application of the first laser radiation pulses for generating the incision in the cornea is combined with the application of the second laser radiation pulses for reshaping the cornea and changing its refractive properties, and controlling the application of the second laser radiation pulses for removing the undesired grating structures in the second region of the cornea are combined in the single computer program executable by the controller.

8. The apparatus according to claim 1, wherein controlling the application of the first laser radiation pulses for generating the incision in the cornea, controlling the application of the second laser radiation pulses for reshaping the cornea and changing its refractive properties, and controlling the application of the second laser radiation pulses for removing the undesired grating structures in the second region of the cornea are each part of a separate computer program executable by the controller.

9. The apparatus of claim 1, wherein controlling control the application of the second laser radiation pulses for removing the undesired grating structures in the second region of the cornea to minimize the undesired rainbow glare effect of the eye without causing undesired changes in the first region of the cornea and without changing the refractive properties of the eye, wherein the removing the undesired grating structures includes removing a volume from the second region of the cornea but not the first region of the cornea, and wherein the first region and second region do not overlap further comprises:
    removing the volume from the second region of the cornea, the volume corresponding to a depth of 15 µm to 20 µm across the second region.

10. An apparatus for laser in-situ keratomileusis (LASIK), comprising:
- a first laser radiation source;
- a second laser radiation source separate from the first laser radiation source and having a lower power density than the first laser radiation source;
- a controller in communication with the first and second laser radiation sources, the controller configured to control operation of the first and second laser radiation sources to control application of laser radiation to an eye from the first and second laser radiation sources, wherein the controller controls operation of the first and second laser radiation sources such that:
    - laser radiation from the first laser radiation source is utilized to form a flap incision in a cornea of the eye to expose a stromal surface, the laser radiation from the first laser radiation source resulting in the formation of undesired grating structures in central and marginal regions of the cornea causing an undesired rainbow glare effect of the eye;
    - after formation of the flap incision, laser radiation from the second laser radiation source is utilized to remove an ablation volume of corneal tissue in the central region of the cornea to change the refractive properties of the cornea in a desired manner to correct myopia, wherein the removal of the ablation volume removes the undesired grating structures from the central region of the cornea, but not from the marginal region of the cornea such that the undesired grating structures remain in the marginal region of the cornea; and
    - after removal of the ablation volume of the corneal tissue in the central region of the cornea, laser radiation from the second laser radiation source is utilized to smooth the exposed stromal surface in the marginal region of the cornea, and not the central region of the cornea, to remove the undesired grating structures in the marginal region of the cornea to minimize the undesired rainbow glare effect of the eye without causing undesired changes in the central region of the cornea and without changing the refractive properties of the eye, wherein the central region includes the exposed stromal surface spaced from the flap incision, wherein the marginal region includes the exposed stromal surface adjacent to the flap incision, and wherein the central region and the marginal region do not overlap.

11. The apparatus of claim 10, wherein the first laser radiation source is a femtosecond laser.

12. The apparatus of claim 11, wherein the second laser radiation source is an excimer laser.

13. The apparatus of claim 10, wherein the controller is configured to control operation of the first and second laser radiation sources such that the laser radiation from the second laser radiation source utilized to remove the ablation volume of corneal tissue causes the radius of curvature of the cornea to be increased.

14. The apparatus of claim 10, wherein the ablation volume is calculated to achieve a desired refractive effect by taking into account the removal of tissue in the marginal region of the cornea to remove the regular corneal surface structures.

15. The apparatus of claim 10, wherein the removal of tissue in the marginal region of the cornea to remove the regular corneal surface structures comprises resecting a tissue layer having thickness up to 10 μm.

16. The apparatus of claim 10, wherein utilizing laser radiation from the second laser radiation source to remove the ablation volume of corneal tissue in the central region of the cornea, and utilizing laser radiation from the second laser radiation source to smooth the exposed stromal surface in the marginal region of the cornea are combined in a single computer program executable by the controller.

17. The apparatus of claim 16, wherein utilizing laser radiation from the first laser radiation source to form the flap incision in the cornea of the eye is combined with utilizing laser radiation from the second laser radiation source to remove the ablation volume of the corneal tissue in the central region of the cornea, and utilizing laser radiation from the second laser radiation source to smooth the exposed stromal surface in the marginal region of the cornea in the single computer program executable by the controller.

18. The apparatus of claim 10, wherein utilizing laser radiation from the first laser radiation source to form the flap incision in the cornea of the eye, utilizing laser radiation from the second laser radiation source to remove the ablation volume of the corneal tissue in the central region of the cornea, and utilizing laser radiation from the second laser radiation source to smooth the exposed stromal surface in the marginal region of the cornea are each part of a separate computer program executable by the controller.

19. The apparatus of claim 10, wherein after removal of the ablation volume of the corneal tissue in the central region of the cornea, laser radiation from the second laser radiation source is utilized to smooth the exposed stromal surface in the marginal region of the cornea, and not the central region of the cornea, to remove the undesired grating structures in the marginal region of the cornea to minimize the undesired rainbow glare effect of the eye without causing undesired changes in the central region of the cornea and without changing the refractive properties of the eye, wherein the central region includes the exposed stromal surface spaced from the flap incision, wherein the marginal region includes the exposed stromal surface adjacent to the flap incision, and wherein the central region and the marginal region do not overlap further comprises:
    - removing the undesired grating structures in the marginal region by removing a volume corresponding to a depth of 15 μm to 20 μm across the marginal region.

20. An apparatus for laser in-situ keratomileusis (LASIK), comprising:
- a first laser radiation source;
- a second laser radiation source separate from the first laser radiation source and having a lower power density than the first laser radiation source;
- a controller in communication with the first and second laser radiation sources, the controller configured to control operation of the first and second laser radiation sources to control application of laser radiation to an eye from the first and second laser radiation sources, wherein the controller controls operation of the first and second laser radiation sources such that:
    - laser radiation from the first laser radiation source is utilized to form a flap incision in a cornea of the eye to expose a stromal surface, the laser radiation from the first laser radiation source resulting in the formation of undesired grating structures in central and marginal regions of the cornea causing an undesired rainbow glare effect of the eye;
    - after formation of the flap incision, laser radiation from the second laser radiation source is utilized to remove an ablation volume of corneal tissue in the marginal region of the cornea to change the refractive properties of the cornea in a desired manner to correct hyperopia, wherein the removal of the ablation volume removes the undesired grating structures from the marginal region of the cornea, but not from the central region of the cornea such that the undesired grating structures remain in the central region of the cornea; and after removal of the ablation volume of the corneal tissue in the marginal region of the cornea, laser radiation from the second laser radiation source is utilized to smooth the exposed stromal surface in the central region of the cornea, and not the marginal region of the cornea, to remove the undesired grating structures in the central region of the cornea to minimize the undesired rainbow glare effect of the eye without causing undesired changes in the marginal region of the cornea and without changing the refractive properties of the eye, wherein the central region includes the exposed stromal surface spaced from the flap incision, wherein the marginal region includes the exposed stromal surface adjacent to the flap incision, and wherein the central region and the marginal region do not overlap.

21. The apparatus of claim 20, wherein the controller is configured to control operation of the first and second laser radiation sources such that the laser radiation from the second laser radiation source utilized to remove the ablation volume of corneal tissue causes the radius of curvature of the cornea to be decreased.

22. The apparatus of claim 20, wherein after removal of the ablation volume of the corneal tissue in the marginal region of the cornea, laser radiation from the second laser radiation source is utilized to smooth the exposed stromal surface in the central region of the cornea, and not the marginal region of the cornea, to remove the undesired grating structures in the central region of the cornea to minimize the undesired rainbow glare effect of the eye without causing undesired changes in the marginal region of the cornea and without changing the refractive properties of the eye, wherein the central region includes the exposed stromal surface spaced from the flap incision, wherein the marginal region includes the exposed stromal surface adjacent to the flap incision, and wherein the central region and the marginal region do not overlap further comprises:

removing the undesired grating structures in the central region by removing a volume corresponding to a depth of 15 μm to 20 μm across the central region.

* * * * *